United States Patent
Long et al.

(10) Patent No.: US 11,375,888 B2
(45) Date of Patent: Jul. 5, 2022

(54) INTRAORAL THREE-DIMENSIONAL SCANNING SYSTEM BASED ON STEREO VISION USING A MONOCULAR CAMERA

(71) Applicant: YUNNAN OBSERVATORIES, CHINESE ACADEMY OF SCIENCES, Yunnan (CN)

(72) Inventors: Qian Long, Yunnan (CN); Pan Ou, Yunnan (CN); Li Zhao, Yunnan (CN); Qiwei Xie, Yunnan (CN); Zicheng Zhao, Yunnan (CN)

(73) Assignee: YUNNAN OBSERVATORIES, CHINESE ACADEMY OF SCIENCES, Kunming (CN)

( * ) Notice: Subject to any disclaimer, the term of this patent is extended or adjusted under 35 U.S.C. 154(b) by 0 days.

(21) Appl. No.: 17/036,183

(22) Filed: Sep. 29, 2020

(65) Prior Publication Data

US 2021/0093178 A1    Apr. 1, 2021

(30) Foreign Application Priority Data

Sep. 29, 2019    (CN) .......................... 201910947140.2

(51) Int. Cl.
*A61B 1/247*    (2006.01)
*G02B 26/10*    (2006.01)

(52) U.S. Cl.
CPC ............ *A61B 1/247* (2013.01); *G02B 26/105* (2013.01)

(58) Field of Classification Search
USPC .......................................... 348/45
See application file for complete search history.

(56) References Cited

U.S. PATENT DOCUMENTS

| | | | |
|---|---|---|---|
| 5,691,839 A * | 11/1997 | Kobayashi | G02B 21/0048 348/E3.053 |
| 5,976,071 A * | 11/1999 | Sekiya | A61B 1/055 600/111 |
| 2005/0089214 A1* | 4/2005 | Rubbert | G01B 11/2504 382/154 |
| 2018/0281757 A1* | 10/2018 | Matsuo | G06K 9/00805 |
| 2019/0208109 A1* | 7/2019 | Hayasaka | G06T 5/003 |

FOREIGN PATENT DOCUMENTS

| CN | 102008282 A | 4/2011 |
|---|---|---|
| CN | 205562955 U | 9/2016 |

* cited by examiner

*Primary Examiner* — Behrooz M Senfi

(57) ABSTRACT

An intraoral three-dimensional scanning system with a monocular camera includes the monocular camera. A first mirror and a second mirror perpendicular to each other are provided between the monocular camera and an object to be measured. A bisector of an angle formed by the first mirror and the second mirror is perpendicular to a lens of the monocular camera, and reflecting surfaces of the first mirror and the second mirror face the lens. A third mirror is provided at a side of the first mirror away from the second mirror, and a fourth mirror is provided at a side of the mirror away from the first mirror. The first mirror, the second mirror, the third mirror and the fourth mirror are located in the same plane.

9 Claims, 2 Drawing Sheets

INTRAORAL THREE-DIMENSIONAL SCANNING SYSTEM BASED ON STEREO VISION USING A MONOCULAR CAMERA

CROSS-REFERENCE TO RELATED APPLICATIONS

This application claims the benefit of priority from Chinese Patent Application No. 201910947140.2, filed on Sep. 29, 2019. The content of the aforementioned applications, including any intervening amendments thereto, is incorporated herein by reference in its entirety.

TECHNICAL FIELD

The application relates to intraoral medical equipment, and more particularly to an intraoral three-dimensional scanner system with a monocular camera.

BACKGROUND

Currently, three-dimensional measurement technologies are widely applied in various industries due to its rapid development. In a digitalization process of dental impressions, three-dimensional information of an object to be measured is generally obtained through computer vision technology. Therefore, scenes to be measured are required to be measured from multiple views to obtain more complete measurement data, or three-dimensional information of the scenes are directly measured through binocular measurement.

Binocular stereoscopic vision fuses images obtained by two cameras to observe the difference between the images, so as to clearly observe a depth and establish a corresponding relation among features. This allows the image points of the same spatial physical point in different images to be mapped. The difference is called disparity.

Measurement methods based on the binocular stereoscopic vision have the advantages of high efficiency, appropriate accuracy, relatively simple system structure, and low cost, which is suitable for online and non-contact product inspection and quality control. Moreover, since images are instantaneously obtained, the binocular stereoscopic vision is a more effective measurement method for moving objects such as animals and human bodies. Binocular stereoscopic vision systems are one of the key technologies of computer vision, and obtaining distance information of three-dimensional scenes is an important content in computer vision research.

However, due to the large size of the apparatus, the binocular stereoscopic vision measurement is limited in some small spaces, such as oral cavities. In addition, monocular cameras are usually unable to obtain complete three-dimensional data due to restrictions of the measurement apparatus and conditions.

In order to solve the problems above, in terms of binocular measurement, the common solution is to reduce sizes of optical lens or shorten baselines. However, reducing the size of the optical lens usually leads to decline in the resolution, and shortening the baseline may reduce the measurement accuracy, which significantly affects the reconstruction of three-dimensional models. For the monocular measurement, higher resolution and more intensive sampling are required, and accordingly the level of algorithm and computing power should be improved.

Therefore, it is urgent to provide a solution to allow micro-cavity scenes in which the binocular measurement is not available, such as oral cavities, intestinal canals and vessels, to be reconstructed through the binocular measurement while allowing the measurement accuracy and the completeness to be theoretically far higher than the traditional monocular measurement under the same computing power.

SUMMARY

In view of the problems in the prior art, the present disclosure provides an intraoral three-dimensional scanner system, comprising a monocular camera;

wherein a first mirror M2 and a second mirror M3 perpendicular to each other are provided between the monocular camera and an object to be measured; a bisector of an angle formed by the first mirror M2 and the second mirror M3 is perpendicular to a lens of the monocular camera, and reflecting surfaces of the first mirror M2 and the second mirror M3 face the lens; a third mirror M1 is provided at a side of the first mirror M2 away from the second mirror M3, and a fourth mirror M4 is provided at a side of the mirror M3 away from the first mirror M2; the first mirror M2, the second M3, the third mirror M1 and the fourth mirror M4 are located in the same plane.

In some embodiments, the first mirror M2, the second mirror M3, the third mirror M1 and the fourth mirror M4 are squares having a side length of 2-5 mm.

In some embodiments, a distance from the lens to an intersection of the first mirror M2 and the second mirror M3 is 1 mm.

In some embodiments, a distance between the third mirror M1 and the first mirror M2 is 3-5 mm, and a distance between the fourth mirror M4 and the second mirror M3 is 3-5 mm.

In some embodiments, an included angle between the third mirror M1 and the bisector is 25-40°, and an included angle between the fourth mirror M4 and the bisector is 25-40°.

The present disclosure further provides a three-dimensional scanning method using the intraoral three-dimensional scanner system, comprising:

carrying out three-dimensional scanning based on binocular stereoscopic vision using the monocular camera and an optical beam splitter or a mirror group;

allowing images of an object surface to reach two opposite target surfaces of the monocular camera through two optical paths by the optical beam splitter; and analyzing the images to obtain cloud data of three-dimensional points of the object surface.

In some embodiments, the intraoral three-dimensional scanning method further comprises:

configuring a red filter between the third mirror M1 and the fourth mirror M4, wherein the red filter is perpendicular to a direction of a beam;

configuring a blue filter between the second mirror M3 and the fourth mirror M4, wherein the blue filter is perpendicular to the direction of the beam and is symmetrical to the red filter;

changing a single channel of a sensor S into red, green and blue (RGB) channels;

acquiring first data through the red channel; and acquiring second data through the blue channel;

carrying out stereo matching for the first data and the second data to obtain disparity information; and converting the disparity information into distance information according to parameters of the lens to realize three-dimensional construction.

In some embodiments, a polarizing filter parallel to the sensor S is provided between the third mirror M1 and the object P and between the fourth mirror M4 and the object P in the two optical paths.

The present disclosure further provides computer equipment, comprising a memory having a computer program stored thereon and a processor; wherein the computer program, when executed by the processor, causes the processor to perform steps of:

carrying out three-dimensional scanning based on binocular stereoscopic vision using the monocular camera and an optical beam splitter or a mirror group;

allowing images of an object surface to reach two opposite target surfaces of the monocular camera through two optical paths by the optical beam splitter; and analyzing the images to obtain cloud data of three-dimensional points of the object surface.

The present disclosure also provides a non-transitory computer-readable storage medium having a computer program stored thereon; wherein the computer program, when executed by a processor, causes the processor to perform steps of:

carrying out three-dimensional scanning based on binocular stereoscopic vision using the monocular camera and an optical beam splitter or a mirror group;

allowing images of an object surface to reach two opposite target surfaces of the monocular camera through two optical paths by the optical beam splitter; and analyzing the images to obtain cloud data of three-dimensional points of the object surface.

The present disclosure further provides a binocular stereoscopic vision system, comprising the intraoral three-dimensional scanner system.

The present disclosure further provides a computer vision system, comprising the intraoral three-dimensional scanner system.

The present invention has the following advantages. Three-dimensional scanning based on binocular stereoscopic vision is carried out using the monocular camera and an optical beam splitter or a mirror group. Images of the object surface reach two opposite target surfaces of the monocular camera through two optical paths by the optical beam splitter; and the images are analyzed to obtain cloud data of three-dimensional points of the object surface. In addition, the size and cost of the scanner system are effectively reduced.

BRIEF DESCRIPTION OF THE DRAWINGS

In order to more clearly explain the technical solutions of embodiments of the present application, the accompanying drawings of the present disclosure will be described as follows. Obviously, the drawings described below are only some embodiments of the present application. For those of ordinary skill in the art, other drawings can be obtained based on the accompanying drawings without paying any creative efforts.

DETAILED DESCRIPTION OF EMBODIMENTS

In order to render the objects, technical solutions and beneficial effects of the invention clearer, the invention will be described below in detail in conjunction with embodiments. It should be understood that these embodiments are merely illustrative of the disclosure, and are not intended to limit the disclosure.

The present disclosure provides an intraoral three-dimensional scanner system, which will be described below in detail in conjunction with the accompanying drawings.

Figure 1:
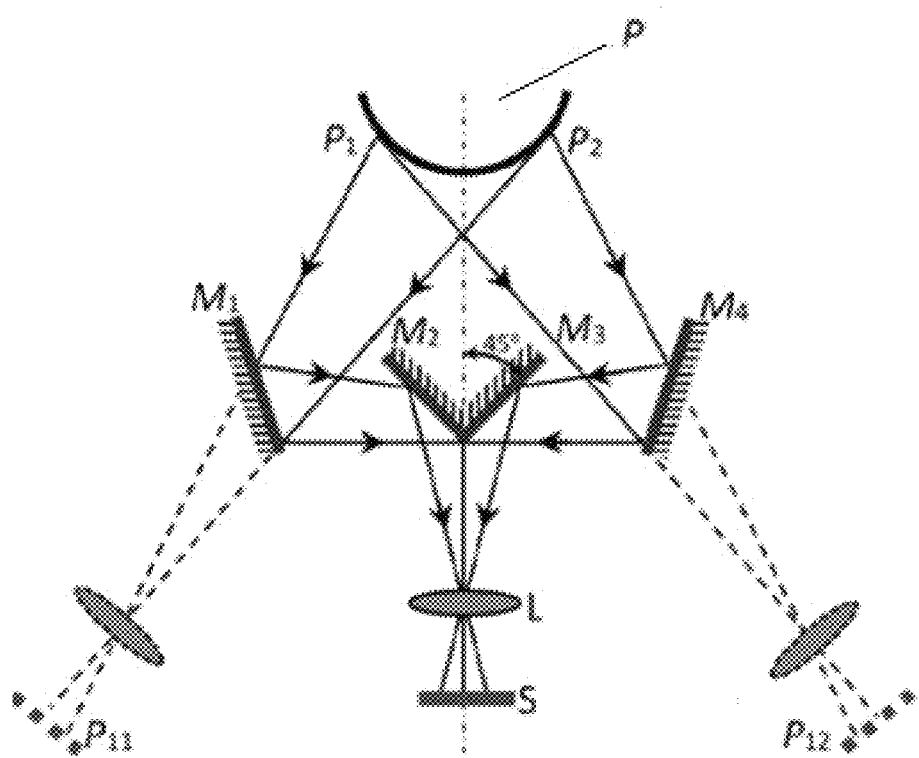
FIG. 1 shows optical paths of an intraoral three-dimensional scanner system with a monocular camera.
Figure 2:
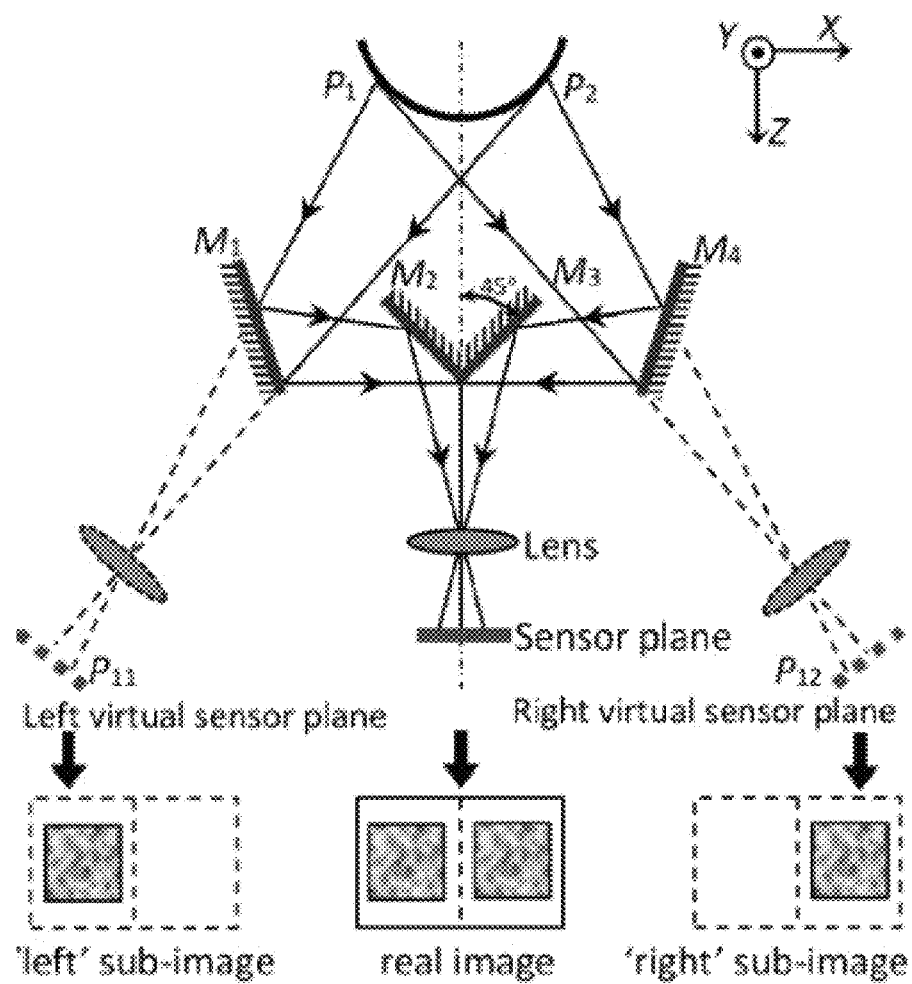
FIG. 2 schematically shows a principle of the intraoral three-dimensional scanner system according to an embodiment of the present disclosure.

As shown in FIG. 1, the intraoral three-dimensional scanner system includes a monocular camera. A first mirror M2 and a second mirror M3 perpendicular to each other are provided between the monocular camera and an object to be measured P; a bisector of an angle formed by the first mirror M2 and the second mirror M3 is perpendicular to a lens L of the monocular camera, and reflecting surfaces of the first mirror M2 and the second mirror M3 face the lens L; a third mirror M1 is provided at a left side of the first mirror M2, and a fourth mirror M4 is provided at a right side of the second mirror M3; the first mirror M2, the second mirror M3, the third mirror M1, and the fourth mirror M4 are located in a same plane.

The first mirror M2, the second mirror M3, the third mirror M1, and the fourth mirror M4 each are squares having a side length of 5 mm. A distance from the lens to an intersection of the first mirror M2 and the second mirror M3 is 1 mm. A distance between the third mirror M1 and the first mirror M2 is 3 mm, and a distance between the fourth mirror M4 and the second mirror M3 is 3 mm. An included angle between the fourth mirror M1 and the bisector of the angle is 30°, and an included angle between the fourth mirror M4 and the bisector of the angle is 30°. These parameters can be adjusted according to actual requirements of products, but the optical paths must be strictly symmetrical.

The intraoral three-dimensional scanner system further includes: optical paths generated by a mirror group; three-dimensional imaging based on binocular stereoscopic vision; a structure light with laser speckles; stereo matching; wireless data communication; and a high-speed implementation based on graphic processing unit (GPU).

In some embodiments, a filter is configured in each of the optical paths. For example, as shown in FIG. 1, a red filter is provided between the fourth mirror M1 and the first mirror M2 and is perpendicular to a direction of light, and a blue filter is provided between the second mirror M3 and the fourth mirror M4 and is symmetrical to the red filter. A single channel of a sensor S is changed to red, green, and blue (RGB) channels. The red channel obtains data of a left optical path, and the blue channel obtains data of a right optical path. Stereo matching is carried out for the data of the left optical path and the data of the right optical path to obtain the disparity information, and the three-dimensional reconstruction is realized by converting the disparity information into distance information according to parameters of the lens. The advantage is that the angle between M3 and M4 can be appropriately increased to make the left and right optical paths overlap on the sensor S, so that the field of view of the left and right optical paths is expanded from half area of S to whole S.

In practical applications, a polarizing filter can be configured in the optical paths to reduce the measurement error caused by the specular reflection of the object. For example, as shown in FIG. 1, a polarizing filter parallel to S is provided between the third mirror M1 and the object P and between the fourth mirror M4 and the object P.

In the description of the present disclosure, "a plurality" means two or more unless otherwise specified. Terms "upper", "lower", "left", "right", "inner", "outer", "front", "rear", "head", "tail", and the like, indicate orientations or positional relationships shown in the drawings, which are merely for ease of description, and are not intended to indicate or imply that the device or element referred to must have a particular orientation or be constructed or operated in a particular orientation, thus should not be construed as limiting the present disclosure. Furthermore, terms "first," "second," "third," and the like are used for descriptive purposes only and should not be interpreted as indicating or implying relative importance.

It should be noted that the embodiments of the present disclosure can be implemented by hardware, software, or a combination thereof. The hardware can be implemented using dedicated logic; the software can be stored in a memory and executed by an appropriate instruction execution system, such as a microprocessor or dedicated hardware. Those of ordinary skill in the art can understand that the above-mentioned devices and methods can be implemented using computer-executable instructions and/or control codes included in the processor. Such codes are provided, for example, in a carrier medium such as a disk, CD or DVD-ROM, or programmable memory such as read-only memory (firmware), or a data carrier such as an optical or electronic signal carrier. The apparatus and its modules of the present disclosure can be implemented by, for example, ultra-large-scale integrated circuits or gate arrays, or semiconductors such as logic chips or transistors, or hardware circuits of programmable hardware devices such as field programmable gate arrays or programmable logic devices. Also, these devices and methods can also be implemented by software executed by various types of processors, or a combination of hardware circuits and software, e.g., firmware.

The above are only the preferred embodiments of the present disclosure, and are not intended to limit the scope of the present disclosure. Any changes, equivalent modifications and improvements based on the concept of the present disclosure and uses in all other related technical fields, shall fall within the protection scope of the present disclosure.

What is claimed is:

1. An intraoral three-dimensional scanner system, comprising a monocular camera;
   wherein the monocular camera consists of one lens, one sensor and a mirror group; the mirror group is provided between the lens and an object to be measured and the mirror group comprises a first mirror M2, a second mirror M3, a third mirror M1 and a fourth mirror M4; the first mirror M2 and the second mirror M3 are perpendicular to each other; a bisector of an angle formed by the first mirror M2 and the second mirror M3 is perpendicular to the lens, and reflecting surfaces of the first mirror M2 and the second mirror M3 face the lens and the sensor; and the lens is arranged between the sensor and the mirror group; the sensor is configured to receive light beams reflected by the mirror group and passing through the lens;
   an included angle between the third mirror M1 and the bisector is less than 45°, and an included angle between the fourth mirror M4 and the bisector is less than 45°, and
   the third mirror M1 is provided at a side of the first mirror M2 away from the second mirror M3, and the fourth mirror M4 is provided at a side of the mirror M3 away from the first mirror M2; the first mirror M2, the second mirror M3, the third mirror M1 and the fourth mirror M4 are located in the same plane.

2. The intraoral three-dimensional scanner system of claim 1, wherein the first mirror M2, the second mirror M3, the third mirror M1 and the fourth mirror M4 are squares having a side length of 2-5 mm.

3. The intraoral three-dimensional scanner system of claim 1, wherein a distance from the lens to an intersection of the first mirror M2 and the second mirror M3 is 1 mm.

4. The intraoral three-dimensional scanner system of claim 1, wherein a distance between the third mirror M1 and the first mirror M2 is 3-5 mm, and a distance between the fourth mirror M4 and the second mirror M3 is 3-5 mm.

5. The intraoral three-dimensional scanner system of claim 1, wherein the included angle between the third mirror M1 and the bisector is 25-40°, and the included angle between the fourth mirror M4 and the bisector is 25-40°.

6. A three-dimensional scanning method using the intraoral three-dimensional scanner system of claim 1, comprising:
   carrying out three-dimensional scanning based on binocular stereoscopic vision using the monocular camera;
   allowing images of an object surface to reach left and right surfaces of the lens through two optical paths by the mirror group; and
   analyzing the images to obtain cloud data of three-dimensional points of the object surface.

7. The intraoral three-dimensional scanning method of claim 6, wherein the sensor has red, green and blue channels; and the intraoral three-dimensional scanning method further comprising:
   configuring a red filter between the third mirror M1 and the first mirror M2, wherein the red filter is perpendicular to a direction of a beam;
   configuring a blue filter between the second mirror M3 and the fourth mirror M4, wherein the blue filter is perpendicular to the direction of the beam and is symmetrical to the red filter;
   acquiring first data through the red channel; and acquiring second data through the blue channel;
   carrying out stereo matching for the first data and the second data to obtain disparity information; and
   converting the disparity information into distance information according to parameters of the lens to realize three-dimensional construction.

8. The intraoral three-dimensional scanning method of claim 6, wherein a polarizing filter parallel to the sensor is provided between the third mirror M1 and the object P and between the fourth mirror M4 and the object P in the two optical paths.

9. A non-transitory computer-readable storage medium having a computer program stored thereon, wherein the computer program, when executed by a processor, causes the processor to perform a method comprising steps of:
   carrying out three-dimensional scanning based on binocular stereoscopic vision using the monocular camera of claim 1;
   allowing images of an object surface to reach left and right surfaces of the lens through two optical paths by the mirror group; and
   analyzing the images to obtain cloud data of three-dimensional points of the object surface.

* * * * *